United States Patent [19]

Kiske et al.

[11] Patent Number: 5,049,317
[45] Date of Patent: Sep. 17, 1991

[54] METERING ARRANGEMENT FOR A GAS MIXTURE

[75] Inventors: Siegfried Kiske, Gross Grönau; Ulrich Palm, Norderstedt, both of Fed. Rep. of Germany

[73] Assignee: Drägerwerk Aktiengesellschaft, Lübeck

[21] Appl. No.: 550,905

[22] Filed: Jul. 11, 1990

[30] Foreign Application Priority Data

Jul. 20, 1989 [DE] Fed. Rep. of Germany ....... 3924123

[51] Int. Cl.$^5$ .............................................. B01F 3/04
[52] U.S. Cl. .......................................... 261/16; 73/3; 73/861.04; 128/203.14; 128/203.25; 128/205.11; 261/19; 261/63; 261/DIG. 65
[58] Field of Search ............. 261/16, 19, 63, DIG. 65; 128/203.14, 203.25, 205.11; 73/3, 861.04

[56] References Cited

U.S. PATENT DOCUMENTS

| | | | |
|---|---|---|---|
| 3,528,418 | 9/1970 | Grosholz et al. | 128/203.14 X |
| 4,091,056 | 5/1978 | Hamalainen et al. | 261/19 |
| 4,341,107 | 7/1982 | Blaie et al. | 73/861.04 X |
| 4,345,612 | 8/1982 | Koni et al. | 128/203.14 X |
| 4,657,710 | 4/1987 | Smith et al. | 261/DIG. 65 |
| 4,770,168 | 9/1988 | Rusz et al. | 128/203.14 X |
| 4,783,343 | 11/1988 | Sato | 261/DIG. 65 |
| 4,798,689 | 1/1989 | Heim et al. | 261/DIG. 65 |

*Primary Examiner*—Richard L. Chiesa
*Attorney, Agent, or Firm*—Walter Ottesen

[57] ABSTRACT

The invention is directed to an arrangement for generating and metering a gas mixture which includes controllable adjusting elements whereby the gas mixture is either conducted through a bypass line past a vaporizer unit to a consumer or is conducted through the vaporizer unit and from there to the consumer. With this arrangement, a calibration of the carrier gas metering especially at low flow quantities is obtained which is continuously reproducible and either carried out manually or automatically without interruption of the metering operation. This is achieved in that a calibrating line opens into a calibrating vessel upstream of the vaporizer unit and the calibrating vessel can be separated by way of shutoff valves from the vaporizer line and a level indicator is connected to the calibrating vessel.

6 Claims, 1 Drawing Sheet

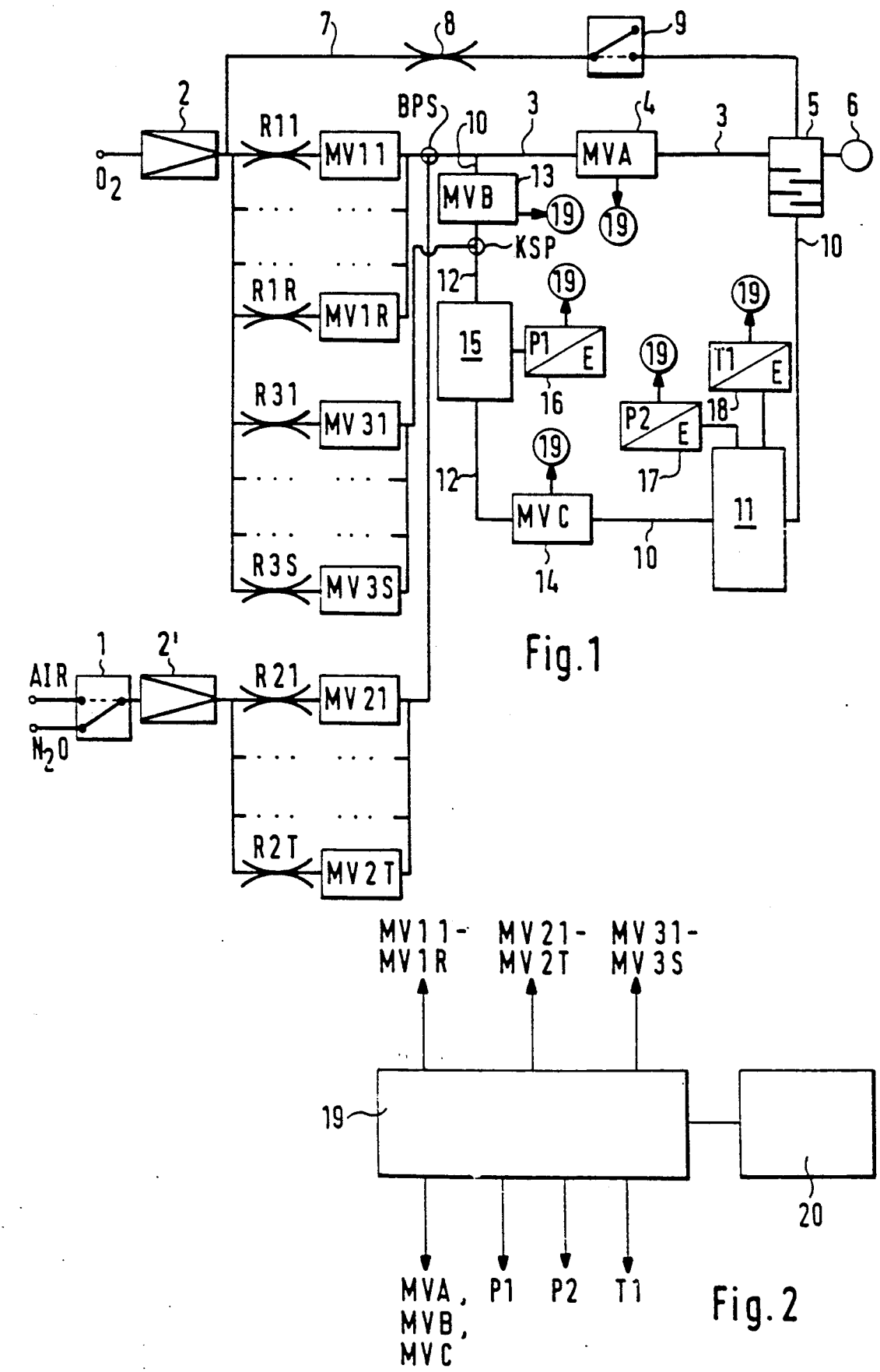

METERING ARRANGEMENT FOR A GAS MIXTURE

FIELD OF THE INVENTION

The invention relates to an arrangement for generating and metering a gas mixture wherein one carrier gas from at least one gas source flows through a supply line via controllable adjusting elements and into a vaporizer unit for adding a fluid into the carrier gas. From there, the carrier gas is conducted into a consumer line with the vaporizer line and the vaporizer unit being bypassable by a bypass line. The carrier gas flow can be conducted past the vaporizer chamber via switching elements.

BACKGROUND OF THE INVENTION

U.S. Pat. No. 4,091,056 discloses an arrangement for vaporizing liquids wherein a carrier gas flow is alternately conducted via a vaporizer or via a bypass line past the vaporizer to the consumer. The flow through the bypass line is conducted through a flow meter having an indicator which can be calibrated to the value zero for the flow then present. The carrier gas entrains a component of the vaporized liquid only when the carrier gas line is switched into the vaporizer whereby the mass flow increases and its increased component is indicated by the flow meter.

The precision of the indicated metered amount on the flow meter is dependent essentially upon how precisely the carrier gas flow is adjusted. The requirements as to the precision of the metering of the carrier gas are better fulfilled at high volume and mass flows than at very low mass flows such as a few milliliters per minute. These low mass flows are then significant when it is intended to supply anesthetic into a closed anesthetic loop from an anesthetic vaporizer. In this way, only such amounts of anesthetic are introduced into the carrier gas which are consumed or removed by possible small leaks from the breathing loop.

SUMMARY OF THE INVENTION

It is an object of the invention to provide an arrangement of the kind described above wherein a continuous and reproducible calibration of the metering of the carrier gas is possible especially for the smallest flow quantities as well as without interrupting the metering operation. It is another object of the invention to provide such an arrangement wherein the calibration can be either carried out automatically or manually.

The arrangement of the invention is for generating and metering a gas mixture to a consumer. The arrangement includes: gas supply means for supplying a carrier gas; adjusting means for receiving the gas and adjusting the metering of the carrier gas; vaporizing means for adding a fluid to the carrier gas; a vaporizer line connecting the adjusting means to the vaporizing means; a bypass line also connected to the adjusting means for conducting the carrier gas past the vaporizing means and the vaporizer line; a switching element connected into the bypass line for opening and closing the bypass line; calibrating means connected into the vaporizer line upstream of the vaporizing means; the calibrating means including: a calibrating vessel; first and second shutoff elements disposed upstream and downstream, respectively, of the calibrating vessel for separating the calibrating vessel from the vaporizer line; and, a level indicator connected to the calibrating vessel.

According to a feature of the invention, a calibrating line opens into a calibrating vessel upstream of the vaporizer unit with the calibrating line being provided with at least one shutoff element. Also, a level indicator is connected to the calibrating vessel.

The advantages of the invention are seen essentially in that the calibrating vessel can first be filled to a desired pressure during a normal switching cycle wherein the carrier gas is conducted through the vaporizer unit. The time needed therefor is detected by a separate time measuring device and the level of the calibrating vessel can then be indicated. This time is then a measure for the metering of the carrier gas. In this way, the adjusted metering can be monitored and corrected. The carrier gas quantity trapped in the calibrating vessel can be conducted into the vaporizer unit after opening the shutoff element. In this way, the vaporized fluid can be introduced into the carrier gas flow precisely in the same manner in which it is possible without carrying out a calibration. After a possible correction of the metering by means of the controllable adjusting elements, the correct quantities are introduced into the corresponding lines with the subsequent switchover operations.

A pressure sensor can be applied as a level indicator. The pressure sensor indicates the content of the calibrating vessel via internal pressure with the dimensions of the vessel being unchangeable. As an alternative, the calibrating vessel can also comprise a pump-cylinder unit with the level indicator being provided by a stroke indicator of the piston.

The calibrating line can either be connected as a closed line to the vaporizer line and be switched off via a shutoff element such as an electromagnetic valve. On the other hand, the calibrating line can be part of the vaporizer line with the calibrating vessel being included in the line chain of the vaporizer line. Shut-off elements are then disposed at the outlet and inlet, respectively, of the calibrating vessel and the shutoff elements can, for example, be electromagnetic valves. In both cases, the calibrating line must be separable from the vaporizer line by shutoff elements. For calibrating the quantity of carrier gas, the calibrating line is then first opened and the further introduction of the carrier gas into the vaporizer unit is blocked. After filling the calibrating vessel, its content is either conducted into the vaporizer unit and from there to the consumer line or, its content is conducted back into the calibrating line and via the switching element into the bypass line and from there conducted to the consumer line without it being conducted through the vaporizer unit. In this way, the selection can be made as to whether the calibration step is either carried out in the course of an additive metering of vaporizer liquid or in the course of a simple conduction of carrier gas to the consumer. The normal metering is therefore not limited by the calibrating step; instead, the metering can be switched in at any desired selectable or automatically controllable points in time. The metering can be corrected in dependence upon the indication of the level indicator.

An automatic operating sequence of the calibration and the possible correction of metering can be achieved in that the adjusting elements are configured as a plurality of parallelly-connected arrangements of supercritical through-flow throttling elements and shutoff valves with the valve outlets being connected together at a collecting point of the supply line. The adjusting elements are actuable by a control unit to which the following are also connected: the switching element, the shutoff elements and the level indicator. A required correction can be performed after carrying out the calibrating step. This correction can be simply performed in that the level indicator supplies the actual value to the control unit and the control unit then compares the actual value with the inputted desired value. The control unit then supplies control signals to the shutoff valves and switches these valves on or off in appropriate numbers in response to corresponding deviation in order to adjust the required metering. Because of the supercritical through-flow throttle elements, the flows are independent of backpressure for an appropriate configuration and, with corresponding weighting of the passthrough capacity of the throttling elements, the metering precision can be obtained with adequate quality by a suitable selection of parallelly-connected throttle elements. The selection of the throttle elements to be connected in is especially simple when the through-flow capability of the throttle elements is provided with a binary weighting. A required correction of the metering can either take place by connecting in the required parallelly-connected shutoff valves or a pregiven number of shutoff elements is pulse-clocked by the control unit with the clock frequency and the pulse width ratio being varied and determined by the control unit.

A second gas source can be provided for metering and calibrating gas mixtures with the corresponding arrangement of throttle elements and shutoff valves being joined at a bypass collecting point into which also a first group of throttle elements and shutoff valves opens which correspond to a first gas source. A predetermined gas mixture in the bypass line can reach the consumer by controlling the corresponding number of shutoff valves. If it is intended to conduct a supplemental dosage of, for example, anesthetic from the vaporizer unit to the consumer, then a second group of throttle elements and shutoff valves associated with a first gas source are directed to a calibration collection point which opens into the calibration line upstream of the vaporizer unit. During the time that the supplemental dosage is conducted to the consumer, only gas from the first gas source flows through the vaporizer unit while a gas mixture of pregiven composition flows through the bypass line. For this purpose, the carrier gas flow through the bypass line as well as the carrier gas flow through the vaporizer unit can be conducted into the calibrating vessel if it is intended to monitor the corresponding metered quantities from both gas sources.

If it is intended to calibrate the gas mixture passing through the bypass line, then the group of shutoff valves and throttle elements which connect into the calibrating collection point are all shut off so that the calibrating vessel can be filled with the gas mixture and its metering controlled when the bypass line is blocked and the calibrating line is open. The vaporizer unit is separated from the calibrating line by the shutoff element connected upstream of the vaporizer unit. After the calibration of the gas mixture is completed, the content of the calibrating vessel is conducted back into the bypass line and to the consumer. If it is intended to calibrate the carrier gas provided for the supplemental metering from the vaporizer unit, the bypass line is separated upstream of the calibrating vessel via the shutoff valve. This carrier gas is conducted from the second group of shutoff valves and the throttle elements of the first gas source to the calibrating collection point. The carrier gas fills the calibrating vessel and the time required therefor is measured. After calibration is completed and possible corrections of the through-flow through the throttle elements, the content of the calibrating vessel is conducted out of the calibrating line into the vaporizer unit which is connected with the calibrating line by the shutoff element connected upstream thereof.

BRIEF DESCRIPTION OF THE DRAWING

The invention will now be described with reference to the drawings wherein:

FIG. 1 is a block diagram of an embodiment of the arrangement according to the invention for generating and metering a gas mixture to a consumer; and FIG. 2 is a block diagram of a control unit for supplying outputs to the arrangement shown in FIG. 1.

DETAILED DESCRIPTION OF THE PREFERRED EMBODIMENTS OF THE INVENTION

The metering and calibrating arrangement shown in FIG. 1 is supplied by at least two different gas sources supplying, for example, oxygen and air, respectively. The second gas source can be connected to an alternate gas source such as nitrous oxide. The gas pressure from the gas sources is reduced via pressure reducers (2, 2') corresponding thereto. The first gas source is connected via a bypass line 3 and a mixing chamber 5 to a consumer 6 illustrated schematically. A shutoff element 4 (MVA) is disposed in the bypass line 3. The output of the pressure reducer 2 is connected with the mixing chamber 5 via a flushing line 7. A flushing throttle 8 and a flushing switch 9 are connected in series in the flushing line 7. A vaporizer line 10 branches from the bypass line into the vaporizer unit 11 from which it runs into the mixing chamber 5. A calibrating line 12 is inserted as a portion of the vaporizer line 10 and is separated by shutoff elements (13, 14) (MVB, MVC).

A calibrating vessel 15 is inserted between the shutoff elements (13, 14). A pressure sensor 16 in the form of a level indicator is connected to the calibrating vessel 15. The pressure and the temperature in the vaporizer unit 11 are sensed by the pressure sensor 17 and the temperature sensor 18. The first gas source from the pressure reducer 2 is conducted via a plurality of series circuits connected in parallel with each series circuit including a throttle element (R1R, R3S) and a shutoff valve (MV1R, MV3S). The first group (MV1R) is connected together from these series circuits to a bypass collection point (BPS) in the bypass line 3 and the second group (MV3S) is connected together in a calibrating collection point (KSP) between the shutoff element 13 (MVB) and the calibrating vessel 15. The second gas source from the pressure reducer 2' is connected upstream of a further parallel circuit of several series circuits of throttle elements (R2T) and shutoff valves (MV2T). These are likewise connected together to the bypass collection point (BPS). The individual shutoff valves (MV1R, MV2T, MV3S) as well as the shutoff elements (4, 13, 14) are actuable via the control unit 19 shown in FIG. 2 to which the level indicator 16 as well as the pressure sensor 17 and the temperature sensor 18 and the shutoff valves (4, 13, 14) are connected. The desired values provided by the user for the metering are inputted via an input unit 20 also shown in FIG. 2. The desired values are converted in the control unit 19 so that the control unit can supply binary coded shutoff valves (MV1R, MV2T, MV3S).

During operation, for example oxygen is supplied from the first gas source in a specific quantity through the bypass line 3 and the mixing chamber 5 to the consumer 6. The gas quantity through the bypass line 3 is determined by a suitable selection of the cutoff valves (MV1R) and the corresponding throttle elements (R1R) switched to the passthrough position. The shutoff valve 4 in the bypass line 3 is opened and the shutoff element 13 in the vaporizer line 10 is closed. A further gas, such as nitrous oxide, is conducted to the bypass collection point (BPS) in the bypass line 3 via the pressure reducer 2'. The quantity of nitrous oxide is determined by the shutoff valves (MV2T) which are switched in. The consumer 6 thereby receives a mixture of oxygen and nitrous oxide, for example, for the purpose of carrying out an anesthesia.

The correct metering can be monitored by initiating a calibrating step. For this purpose, the shutoff valve 4 in the bypass line 3 is closed so that the flow through the bypass line to the mixing chamber 5 is interrupted. At the same time, the shutoff element 13 in the vaporizer line 10 is opened so that the gas mixture from the bypass collection point (BPS) flows into the calibrating vessel 15. The shutoff element 14 downstream of the calibrating vessel 15 remains closed. The calibrating vessel 15 is filled up to a pregiven pressure value which is determined by the level indicator 16. When this pressure value is reached, the time required therefor is determined by the control unit 19 and the shutoff element 4 is opened so that the content of the calibrating vessel 15 can escape into the mixing chamber 5 to the consumer 6. The determined filling time of the calibrating vessel is compared with the desired value provided therefor and, when there is a deviation, the corresponding number of shutoff valves (MV1R, MV2T) can be switched over.

If in addition to the mixture of oxygen and nitrous oxide, it is intended to conduct a further anesthetic gas from the vaporizer unit 11 into the mixing chamber, then oxygen is conducted into the calibrating vessel 15 from the second group of parallelly-connected shutoff valves (MV3S) with the calibrating line 12 being closed at both ends of the calibrating vessel 15 by shutoff valves (13, 14). The calibrating vessel 15 is filled until the filling pressure required for the corresponding dosage volume is determined by the level indicator 16 and transmitted to the control unit 19. If the required dosage volume matches the inputted desired value, the shutoff valve 14 between calibrating vessel 15 and vaporizer unit 11 is opened so that the content of the calibrating vessel 15 can be conducted via the vaporizer unit 11 to the mixing chamber. In this way, the metered quantity of carrier gas (for example oxygen) entrains the quantity of anesthetic gas and conducts it to the consumer 6. After the supplemental metering of additional anesthetic gas is completed, the shutoff valve 14 is again closed and the filling operation of the calibrating vessel 15 starts again. Only if a supplemental metering of anesthetic via the calibrating line 12 is again required, the shutoff element 14 is again opened. If the quantity for filling the calibrating vessel 15 is again not obtained, then an appropriate selection of the shutoff valves (MV3S) to be opened and to be closed by the control unit 19 adjusts the required filling quantity for the calibrating vessel 15.

The shutoff valve 13 remains closed for the entire duration of the supplemental metering of anesthetic gas from the vaporizer unit 11. The anesthetic gas mixture present at the bypass collection point (BPS) can be filled into the mixing chamber 5 via the bypass line 3. However, this quantity is reduced by a component which is conducted into the mixing chamber 5 through the additional metering of oxygen and vaporized anesthesia medium from the vaporizer unit 11. In this way, the total gas quantity of the gas conducted to the consumer 6 is the same. Instead of nitrous oxide, air as a second gas source can be added to the oxygen from the first gas source via the selection switch 1.

It is understood that the foregoing description is that of the preferred embodiments of the invention and that various changes and modifications may be made thereto without departing from the spirit and scope of the invention as defined in the appended claims.

What is claimed is:

1. Arrangement for generating and metering a gas mixture to a consumer, the arrangement comprising:
   gas supply means for supplying a carrier gas;
   adjusting means for receiving the gas and adjusting the metering of said carrier gas;
   vaporizing means for adding a fluid to said carrier gas;
   a vaporizer line connecting said adjusting means to said vaporizing means;
   a bypass line also connected to said adjusting means for conducting said carrier gas past said vaporizing means and said vaporizer line;
   a switching element connected into said bypass line for opening and closing said bypass line;
   calibrating means connected into said vaporizer line upstream of said vaporizing means; said calibrating means including: a calibrating vessel; first and second shutoff elements disposed upstream and downstream, respectively, of said calibrating vessel for separating said calibrating vessel from said vaporizer line; and, a level indicator connected to said calibrating vessel.

2. The arrangement of claim 1, said level indicator being a pressure sensor.

3. The arrangement of claim 2, wherein a quantity of carrier gas is calibrated, the arrangement further comprising:
   control means connected to said switching element, said first shutoff element and said second shutoff element for switching said switching element closed for closing said bypass line and for switching said first shutoff element open to open said vaporizer line into said calibrating vessel and for switching said second shutoff element closed to interrupt the flow of carrier gas into said vaporizing means; and,
   said control means also being connected to said pressure sensor for detecting when said calibrating vessel is filled and for then switching said second shutoff element open while maintaining said first shutoff element closed to permit the contents of said calibrating vessel to flow into and through said vaporizing means to the consumer thereby calibrating the quantity of carrier gas.

4. The arrangement of claim 2, wherein a quantity of carrier gas is calibrated, the arrangement further comprising:
   control means connected to said switching element, said first shutoff element and said second shutoff element for switching said switching element closed for closing said bypass line and for switching said first shutoff element open to open said vaporizer line into said calibrating vessel and for switching said second shutoff element closed to interrupt the flow of carrier gas into said vaporizing means; and, said control means also being connected to said pressure sensor for detecting when said calibrating vessel is filled and for then switching both said switching element and said first shutoff element open while maintaining said second shutoff element closed to permit the contents of said calibrating vessel to flow back through said vaporizer line and into and through said bypass line to the consumer thereby calibrating the quantity of carrier gas.

5. The arrangement of claim 2, further comprising:

said adjusting means including a plurality of parallelly connected series circuits; each of said series circuits including a supercritical through-flow throttle element (R1R) and a shutoff valve (MV1R) connected in series with said throttle element (R1R);

bypass collection point means interposed between said adjusting means and said bypass line and between said adjusting means and said vaporizer line so as to be upstream of both said bypass line and said vaporizer line;

control means for actuating the shutoff valves (MV1R) of said series circuits; and, said first and second shutoff elements, said switching element and said pressure sensor all being connected to said control means.

6. The arrangement of claim 2, further comprising:

said gas supply means being a first gas supply for supplying a carrier gas;

said adjusting means including a first plurality of parallelly connected first series circuits connected to said first gas supply; each of said first series circuits including a through-flow throttle element (R1R) and a shutoff valve (MV1R) connected in series with said throttle element (R1R);

bypass collection point means (BPS) disposed in said bypass line and connected to said first series circuits;

said adjusting means including a second plurality of parallelly connected second series circuits also connected to said first gas supply; each of said second series circuits including a through-flow throttle element (R3S) and a shutoff valve (MV3S) connected in series with said throttle element (R3S);

calibrating collection point means (KSP) connected between said first shutoff element and said calibrating vessel and being connected to said second series circuits;

a second gas supply for supplying a second gas;

ancillary adjusting means for receiving said second gas and adjusting the metering of said second gas;

said ancillary adjusting means including a third plurality of parallelly-connected third series circuits connected to said second gas supply; each of said second series circuits including a through-flow throttle element (R2T) and a shutoff valve (MV2T) connected in series with said throttle element (R2T);

said third series circuits also being connected to said bypass collection point means (BPS);

control means for actuating the shutoff valves of said first, second and third series circuits; and, said first and second shutoff elements, said switching element and said pressure sensor all being connected to said control means.

* * * * *